United States Patent [19]

Bowskill et al.

[11] Patent Number: 4,795,669
[45] Date of Patent: * Jan. 3, 1989

[54] DISPOSABLE PROTECTIVE SHIELD FOR HANDLE OF ILLUMINATION DEVICE

[76] Inventors: Mary J. Bowskill, 3721 Dupont St., Anderson, Calif. 96007; Norman V. McDonald, 4860 Alta Mesa Dr., Redding, Calif. 96002

[*] Notice: The portion of the term of this patent subsequent to Feb. 2, 2005 has been disclaimed.

[21] Appl. No.: 117,953

[22] Filed: Nov. 9, 1987

Related U.S. Application Data

[63] Continuation-in-part of Ser. No. 7,591, Jan. 28, 1987, Pat. No. 4,722,296.

[51] Int. Cl.$^4$ ............................................. B25G 1/02
[52] U.S. Cl. ..................... 428/194; 16/111 R; 16/114 R; 118/504; 118/505; 362/804; 428/40
[58] Field of Search ................. 16/111 R, 114 R; 118/504, 505; 362/804; 428/40, 194, 23

[56] References Cited

U.S. PATENT DOCUMENTS

| 3,785,102 | 1/1974 | Amos | 428/40 X |
| 3,916,447 | 11/1975 | Thompson | 428/284 X |
| 3,961,602 | 6/1976 | Dresser | 428/40 X |
| 4,000,737 | 1/1977 | Horn | 128/154 |
| 4,107,811 | 8/1978 | Imsande | 428/40 X |
| 4,143,194 | 3/1979 | Wihksne | 428/45 X |
| 4,384,382 | 5/1983 | Diamant | 128/62 A |
| 4,386,179 | 5/1983 | Sterling | 604/96 X |
| 4,559,671 | 12/1985 | Andrews | 118/504 X |
| 4,697,544 | 10/1987 | Stevens et al. | 118/504 |
| 4,722,296 | 2/1988 | Bowskill et al. | 428/194 X |

FOREIGN PATENT DOCUMENTS

| 452479 | 5/1968 | Switzerland | 428/194 |
| 1023894 | 3/1966 | United Kingdom | 362/804 |

Primary Examiner—Henry F. Epstein
Attorney, Agent, or Firm—Leonard Bloom

[57] ABSTRACT

A disposable shield for the handle of a light used by dentists or doctors is disclosed. A new shield is used for each patient, thereby preventing the spreading of contagious diseases. The shield includes a flap covering the stem of the handle, thereby providing additional protection.

7 Claims, 7 Drawing Sheets

DISPOSABLE PROTECTIVE SHIELD FOR HANDLE OF ILLUMINATION DEVICE

CROSS REFERENCE TO RELATED APPLICATION

The present application constitutes a continuation-in-part of application Ser. No. 007,591 filed Jan. 28, 1987 now U.S. Pat. No. 4,722,296, issued on Feb. 2, 1988, the disclosure of which is incorporated herein in its entirety.

FIELD OF THE INVENTION

The present invention relates to a disposable protective shield intended to be applied to the handle of a light or other illumination device used for medical and/or dental purposes.

BACKGROUND OF THE INVENTION

With the advent of infectious diseases which are rampant in our society today, particularly Acquired Immunization Deficiency Syndrome (commonly referred to as "AIDS"), many patients simply do not consult their doctor or dentist for fear of contracting the deadly AIDS virus, especially in view of the prognosis that AIDS will reach epidemic proportions in the future. As a result, doctors and dentists have become more vigilant in adhering to precautionary sanitation measures. Dentists as well as dental hygienists, for example, have widely adopted the practice of using a pair of disposable plastic gloves for each patient, so that any saliva, blood or tissue particles that may conceivably carry the deadly AIDS virus bacteria will not be inadvertently transferred from one patient to another. These protective disposable gloves are in addition to washing the hands.

Nevertheless, a dentist frequently manipulates the light during the examination and treatment of a patient; and any saliva, blood or tissue particles picked up on the plastic gloves may be inadvertently transferred to the handle of the light, which unlike the dental instruments, is neither protected nor sanitized from patient to patient.

SUMMARY OF THE INVENTION

Accordingly, it is an object of the present invention to alleviate the disadvantages and deficiencies of th prior art by providing a disposable protective siield for the handle of a light or other illumination device used for medical and/or dental purposes, thereby preventing the inadvertent exposure to and transfer of, a contagious infection from one patient to another.

It is another object of the present invention to provide a disposable protective shield which is economical to manufacture and is easy and convenient to use.

In accordance with the teachings of the present invention, there is herein illustrated and described, a preferred embodiment thereof comprising a disposable protective shield for the handle of an illumination device intended for medical and/or dental purposes. The protective shield comprises a substantially planar flexible sheet having a generally rectangular plan outline including top and bottom sides and further including a perimeter having forward and rear edge and substantially parallel side edges. The forward edge has a cut-out portion formed therein and extending towards the rear edge of the sheet. A band of adhesive is carried on the bottom side of the sheet and extends around the perimeter thereof. With this arrangement, the rear edge of the sheet may be adhesively secured to the handle, temporarily becoming an integral part thereof; and the sheet may then be manually rolled around the handle in substantially close fitting relationship thereto and removably secured thereto. As a result, the sheet will not unravel from the handle of the light during repeated manipulation thereof during the examination of a patient, such that each patient is protected against inadvertent contamination from a previous patient. Thereafter, the sheet may be easily removed from the handle of the light and discarded following examination and treatment of a particular patient in the medical or dental office, clinic or hospital.

Preferably, a stack of sheets is adhesively secured together in a stack, wherein the uppermost sheet may be peeled off the stack and applied to the handle.

In accordance with another aspect to the present invention, there is herein illustrated and described, the combination of an illumination device intended for medical and/or dental purposes, the device having a handle, and a stack of protective shields for the handle. The stack includes a plurality of sheets removably secured together, such that uppermost sheet in the stack may be removed from the stack. Each sheet is relatively thin and flexible and is adapted to be curled around the handle and removably secured thereto; and adhesive means is carried by the sheet for adhering to the handle.

In accordance with the further teachings of the present invention, there is herein illustrated and described, an alternate embodiment thereof comprising a disposable protective shield for the handle of a light intended for use in medical and/or dental offices, the light including a handle having a stem. The shield comprises a substantially planar flexible sheet having a generally rectangular plan outline including top and bottom sides and further including a perimeter having forward and rear edges and substantially parallel side edges. The sheet further has a pair of substantially parallel slits formed therein and extending from the forward edge towards the rear edge, thereby forming a flap. An adhesive is carried on the bottom side of the sheet and extends at least around the perimeter thereof and on the flap along the respective slits. In using the sheet the rear edge thereof may be adhesively secured to the handle, temporarily becoming an integral part thereof, and the sheet may then be manually rolled around the handle of the light in substantially close fitting relationship thereto and removably secured thereto. As a result, the sheet will not unravel from the handle of the light during repeated manipulation thereof during examination of a patient; and the flap will be removably secured on top of the stem of the handle, thereby precluding contact with the stem. Accordingly, each patient is protected against inadvertent contamination from a previous patient; and the sheet may be easily removed from the handle of the light and its stem and thereafter discarded, following examination and treatment of a particular patient in the medical or dental office.

Viewed in yet another aspect, and in combination with an illumination device intended for medical and/or dental purposes, wherein the device includes a handle having a stem, the present invention provides a stack of disposable protective shields for the handle. The stack includes a plurality of sheets removably secured together, such that the uppermost sheet in the stack may be removed from the stack. Each sheet is relatively thin and flexible and is adapted to be curled around the handle and removably secured thereto, and an adhesive means is carried by the sheet for removably adhering the sheet to the handle. Additionally, a flap is formed on the sheet and has an adhesive means carried thereon for removably adhering the flap to the stem of the handle, thereby providing protection against contamination of the stem of the handle.

Preferably, each sheet is substantially rectangular in plan outline and has top and bottom sides and further has a band of adhesive on one of the sides around the perimeter thereof. Each sheet has a forward edge and a rearward edge, and each sheet has a pair of substantially parallel slits formed therein and extending from the forward edge towards the rearward edge, thereby forming the flap on the sheet.

These and other objects of the present invention will become apparent from a reading of the following specification, taken in conjunction with the enclosed drawings.

GENERAL DESCRIPTION OF THE PREFERRED EMBODIMENT

Figure 1:
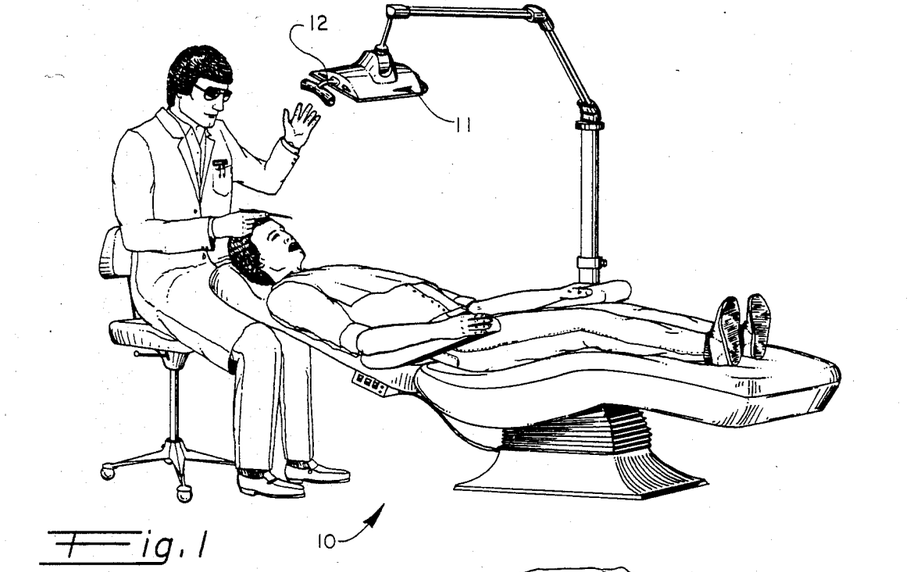
FIG. 1 is a perspective view of a typical dentist's chair, showing the light with its handle, with which the teachings of the present invention may find more particular utility.
Figure 2:
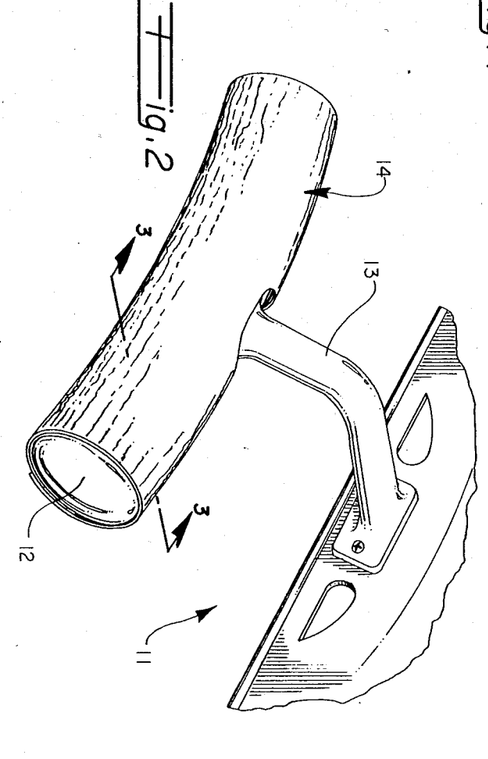
FIG. 2 is a portion of FIG. 1, drawn to an enlarged scale, and showing a disposable protective shield of the present invention removably wrapped around the handle.
Figure 3:
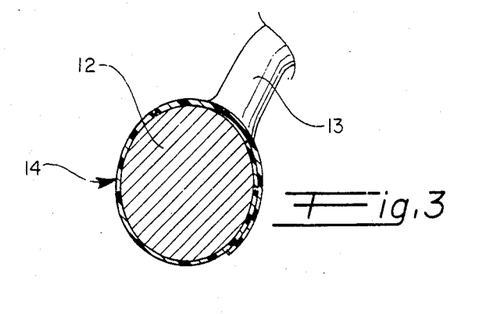
FIG. 3 is a cross-sectional view thereof, taken along the lines 3—3 of FIG. 2, and drawn to an enlarged scale.

With reference to FIGS. 1-3, there is illustrated a typical dentist's chair 10 and light 11 with which the teaching of the present invention may find more particular utility. However, it will be appreciated by those skilled in the art that the invention is not restricted thereto, but is adaptable to other medical or dental uses and to a variety of illumination devices. With this in mind, the light 11 is equipped with a handle 12 which (as shown herein) is carried by a stem 13, thereby forming a "Tee" handle. Wrapped around this Tee handle is the disposable proeective shield 14 of the present invention.

Figure 4:
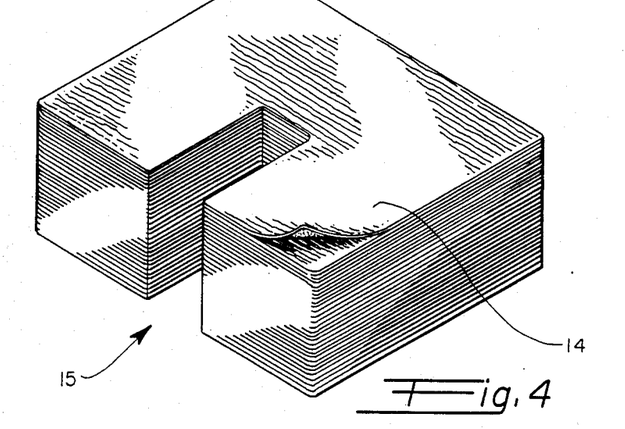
FIG. 4 is a perspective view of the stack of disposable shields of the present invention, showing how the uppermost shield or sheet may be peeled off the stack.
Figure 5:
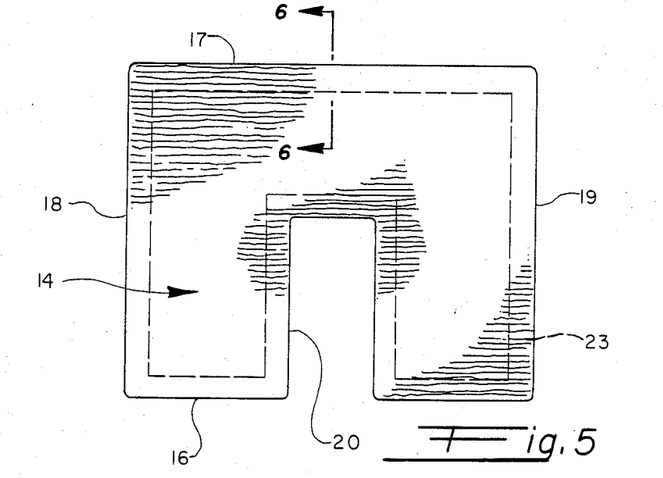
FIG. 5 is a top plan view of one of the sheets.
Figure 6:
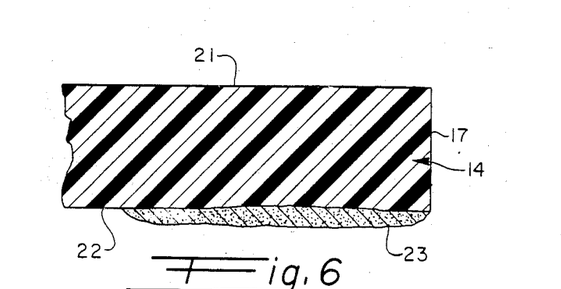
FIG. 6 is a sectional view thereof, taken across the liees 6—6 of FIG. 5, drawn to an enlarged scale, and showing a portion of the adhesive carried by the underside of the sheet and formed as a band around the periphery thereof.

With reference to FIGS. 4-6, the shields 14 are arranged in a stack 15, such that the uppermost shield may be peeled off the stack as shown more clearly in FIG. 4. Each shield 14 comprises a relatively-thin flexible sheet made from any suitable material such as a plastic type of "crepe paper". A suitable material for this purpose is the material used for the patient's headrest. As shown more clearly in FIG. 5, each sheet is preferably rectangular in plan outline and has a forward edge 16, a rear edge 17 and parallel side edges 18 and 19. The forward edge is provided with a slotted cut-out portion 20 adapted to fit around a Tee handle. The sheet further has a top surface or side 21 and an underside 22, as shown in FIG. 6, and a band 23 of adhesive is carried on the underside of each sheet around the perimeter thereof.

In this manner, the stack of disposable shields may be integrally held together, but the top shield may be easily and conveniently removed from the stack and wrapped around the light handle for each patient.

Figure 7:
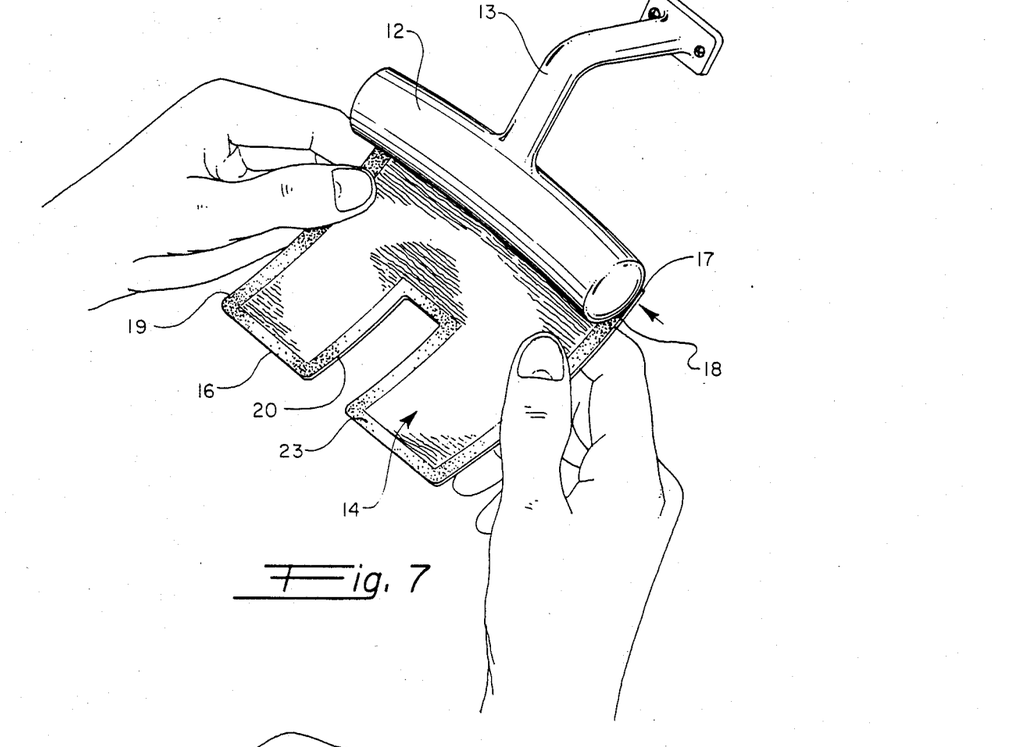
FIGS. 7, 8, and 9 are partial perspective views, showing in sequence the manner in which the protective shield is wrapped around the handle on the light.
Figure 8:
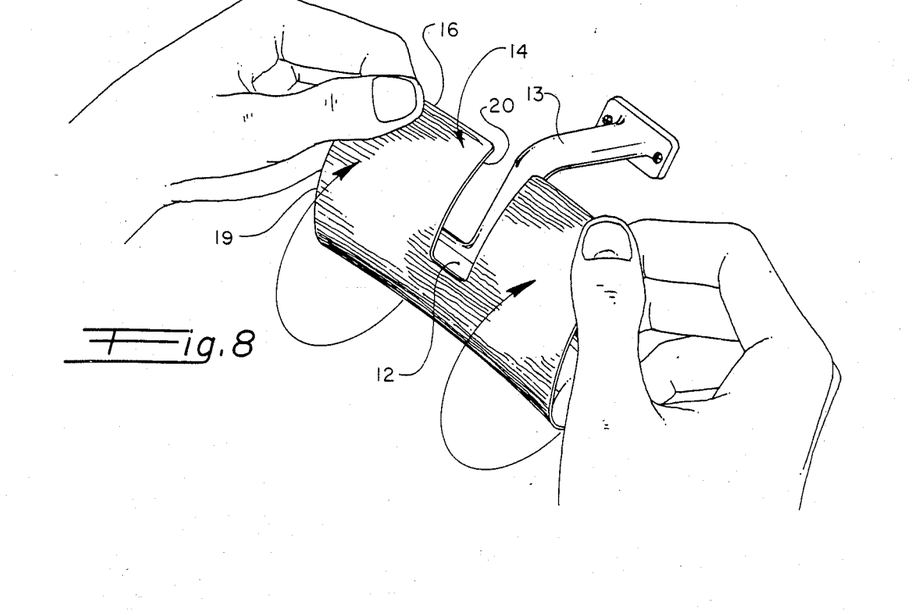
Figure 9:
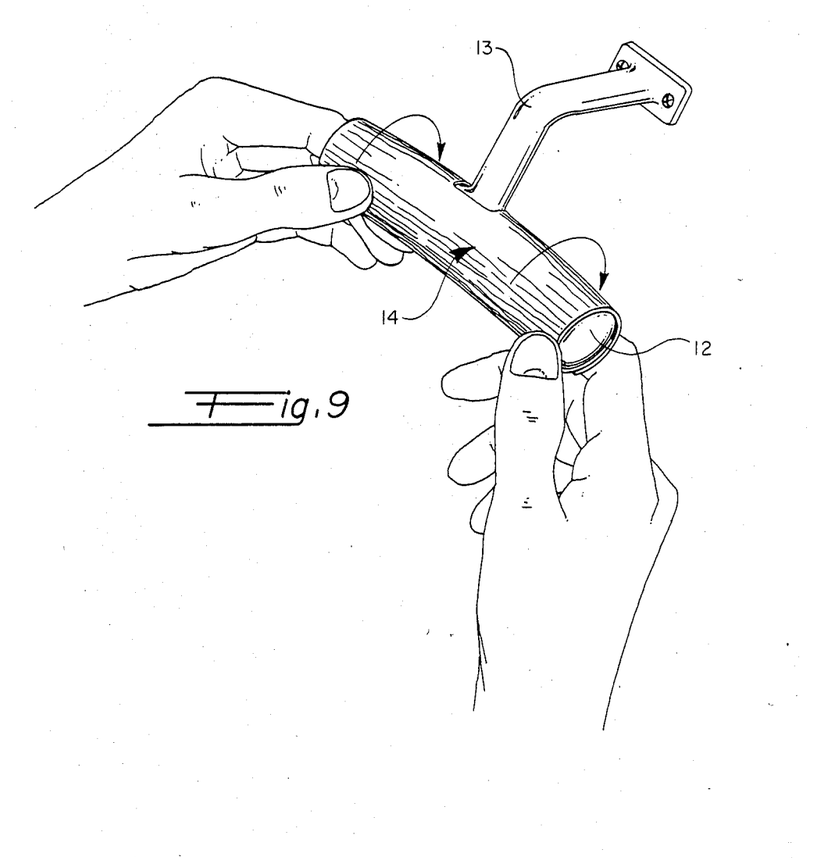

With reference to FIGS. 7-9, the sequence of applying the disposable protective shield 14 to the handle of the light 11 is illustrated. In FIG. 7, the shield 14 has been removed from its stack 15, and the adhesive band 23 on the underside of the shield 15 (at the rear edge 17 thereof) has been applied to the handle 12 to secure the shield 14 thereto, such that the cut-out portion 20 thereof will straddle the stem 13 of the Tee-shaped handle 12. Thereafter, as shown in FIG. 8, the shield 14 is wrapped around the handle 12, progressively, and is removably secured thereto as shown in FIG. 9.

After treatment and/or diagnosis of the patient has been completed, the shield 14 is removed and discarded; and thereafter, a new shield is placed on the handle for the next patient. Thus, regardless of the number of times the doctor may manipulate the handle of the light to cast better illumination upon the area of the particular patient being treated, there is no opportunity for the handle to become inadvertently a carrier for infectious or contagious diseases.

Figure 10:
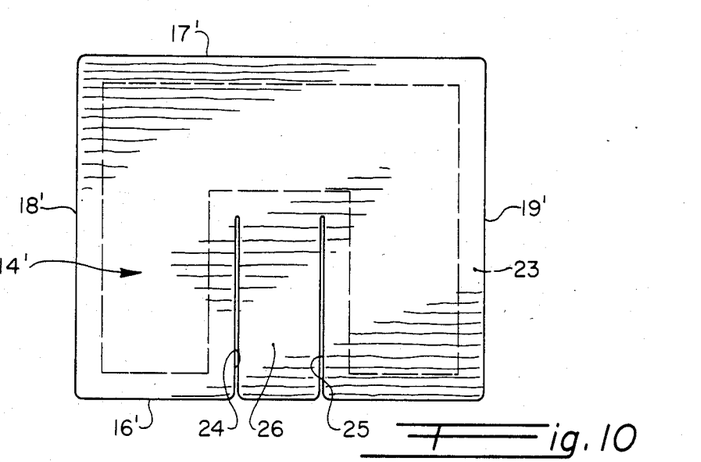
FIG. 10 is a top plan view of an alternate embodiment of the protective shield or sheet of the present invention, wherein a flap is provided in lieu of the cut-out in the embodiment of FIG. 5, the flap being formed by a pair of parallel slits extending from the forward edge of the sheet, and wherein the entire underside of the flap is coated with a suitable adhesive.

With reference to FIG. 10, an alternate embodiment of the present invention is illustrated, wherein the protective shield (or sheet) 14' is preferably rectangular and has a forward edge 16', a rear edge 17' and parallel side edges 18' and 19', respectively. The shield 14' has a pair of substantially parallel slits 24 and 25 formed therein and extending from the forward edge 16' to the rear edge 17', thereby forming a flap 26. Carried on the underside of the shield 14' is a band of adhesive 23' around the perimeter of the shield 14'. The bottom of the flap 26 may be coated entirely with a suitable adhesive.

Figure 11:
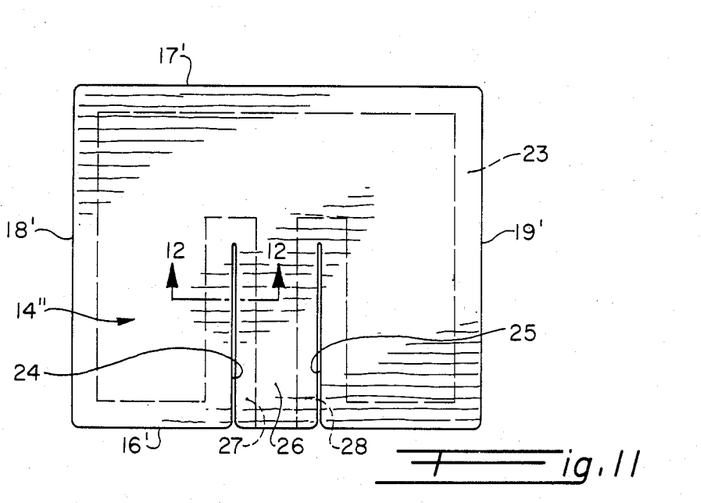
FIG. 11 is a top plan view of a still further embodiment, corresponding substantially to that of FIG. 10, but showing the adhesive on the flap formed only along the sides of the respective slits.
Figure 12:
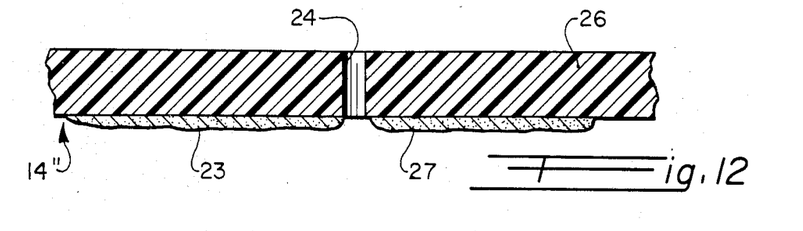
FIG. 12 is a cross-sectional view thereof, taken along the lines 12—12 of FIG. 11 and drawn to an enlarged scale, and showing one of the slits formed in the sheet to thereby form the flap therein.

In the further alternate embodiment of FIG. 11, the sheet 14" is provided with adhesive strips 27 and 28 on the underside of the flap 26, along the slits 24 and 25, respectively.

Figure 13:
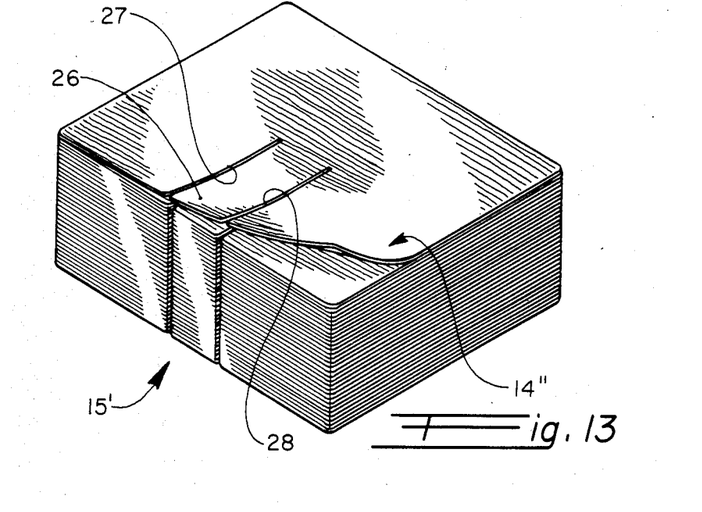
FIG. 13 is a perspective view of a stack of the sheets of FIG. 11, wherein the top sheet is being peeled off the stack.

With reference to FIG. 13, a stack 15' of the shields 14" is illustrated The top shield 14" may be peeled off the stack 15', as desired.

Figure 14:
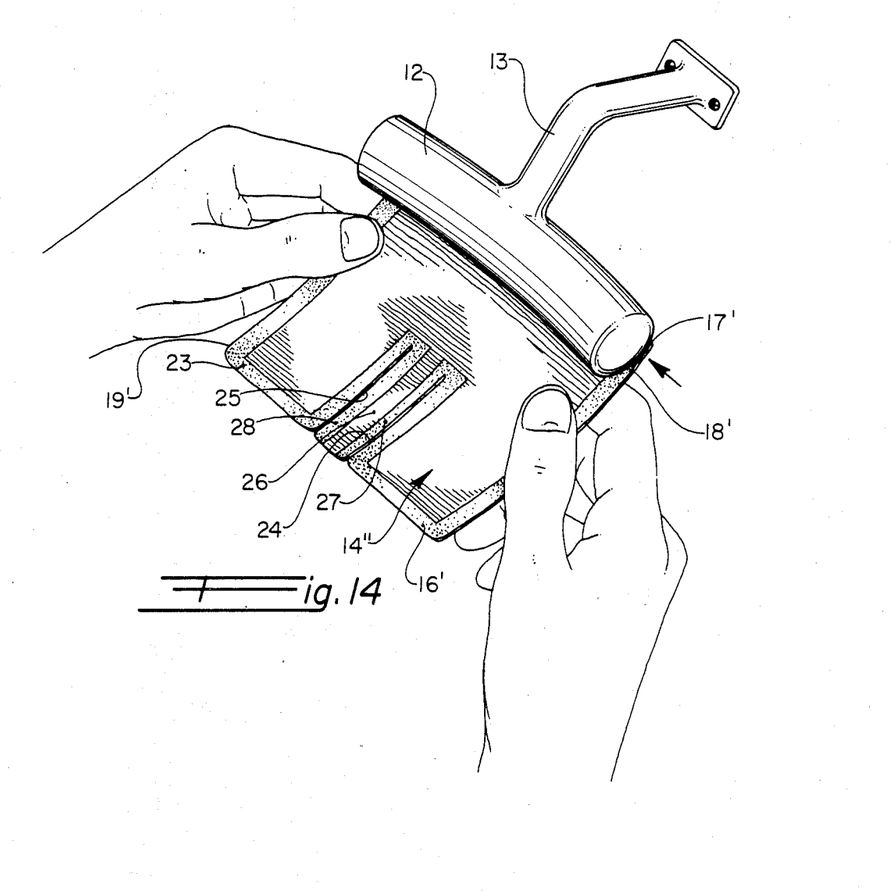
FIGS. 14, 15 and 16 are partial perspective views, corresponding substantially to that of FIGS. 7, 8 and 9, respectively, and showing the manner in which the protective shield of the alternate embodiment of FIG. 11 is wrapped around the handle of the light, and further showing the manner in which the flap on the sheet covers the stem on the handle of the light.
Figure 15:
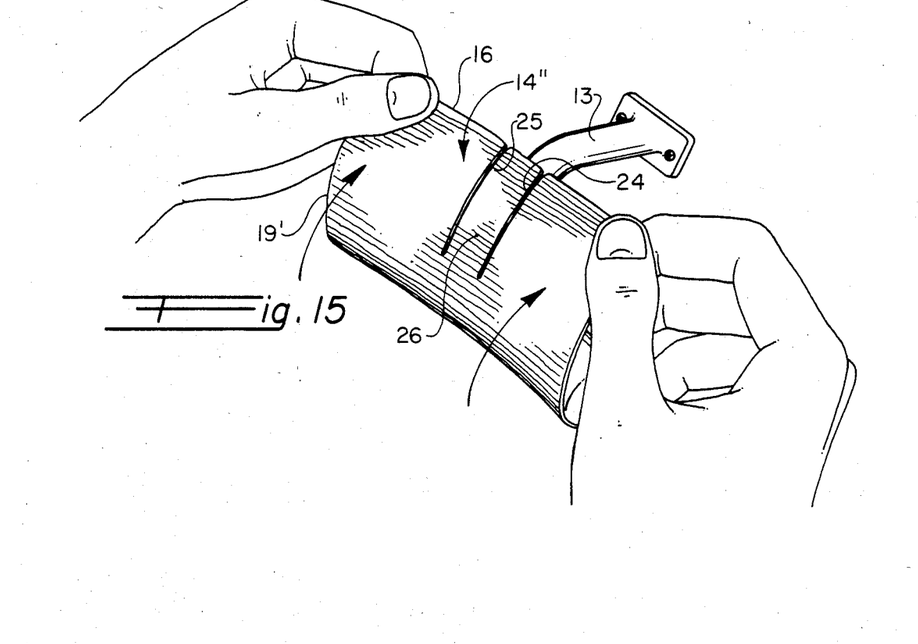
Figure 16:
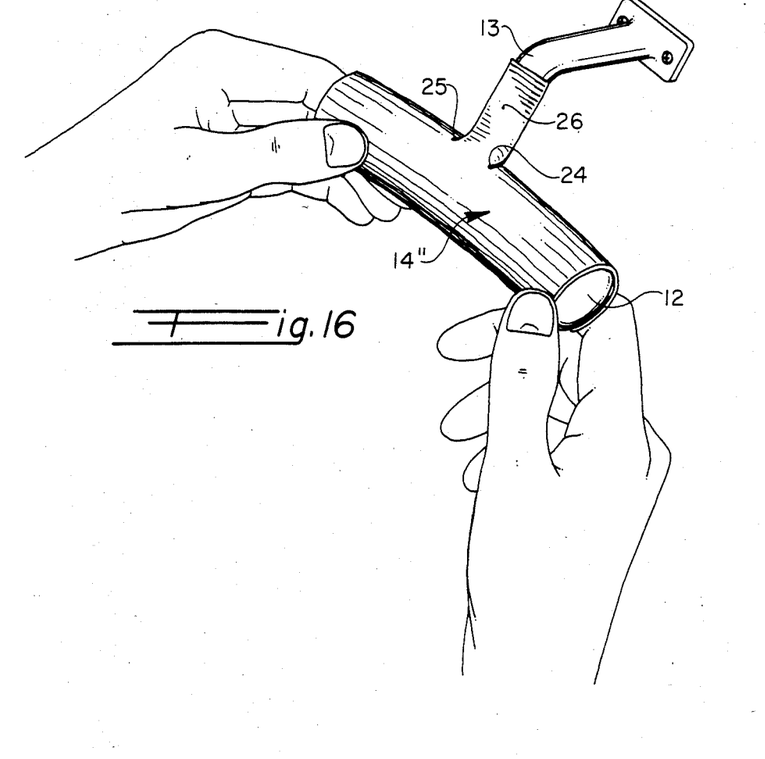

With reference to FIGS. 14, 15 and 16, there is illustrated the sequence of applying the disposable protective shield 14" to the handle of the light 11. In FIG. 14, the shield 14" has been removed from its stack 15' and the adhesive band 23' on the underside of the shield 14" (at the rear edge 17' thereof) has been applied to the handle 12 to secure the shield 14" thereto. Thereafter, as shown in FIG. 15, the shield 14" is manually wrapped around the handle 12, progressively, being removably secured thereto. As shown in FIG. 16, the flap 26 on the shield 14" removably covers the stem 13 and provides additional protection for the patient.

Obviously, many modifications may be made wihhout departing from the basic spirit of the present invention. Accordingly, it will be appreciated by those skilled in the art that within the scope of the appended claims, the invention may be practiced other than has been specifically described herein.

What is claimed is:

1. In combination with a light intended for use in medical and/or dental offices, the light including a handle having a stem, a disposable protective shield for the handle, said shield comprising a substantially planar flexible sheet having a generally rectangular plan outline including top and bottom sides and further including a perimeter having forward and rear edges and substantially parallel side edges, the sheet having a pair of substantially parallel slits formed therein and extending from the forward edge towards the rear edge, thereby forming a flap, and adhesive carried on the bottom side of the sheet and extending at least around the perimeter thereof and on the flap along the respective slits, whereby the rear edge of the sheet may be adhesively secured to the handle, temporarily becoming an integral part thereof, and whereby the sheet may then be manually rolled around the handle of the light in substantially close fitting relationship thereto and removably secured thereto, so that the sheet will not unravel from the handle of the light during repeated manipulation thereof during examination of a patient, and so that the flap will be removably secured on top of the stem of the handle, thereby protecting contamination from contact with the stem, whereby each patient is protected against inadvertent contamination from a previous patient, and whereby the sheet may be easily removed from the handle of the light and its stem and thereafter discarded following examination and treatment of a particular patient in the medical or dental office.

2. The combination of claim 1, further including a stack of sheets adhesively secured together, wherein the uppermost sheet in the stack may be peeled off the stack.

3. In combination with an illumination device intended for medical and/or dental purposes, the device including a handle having a stem, a stack of disposable protective shields for the handle, the stack including a plurality of sheets removably secured together, wherein the uppermost sheet in the stack may be removed from the stack, each sheet being relatively thin and flexible and being adapted to be curled around the handle and removably secured thereto, adhesive means carried by the sheet for removably adhering the sheet to the handle, and a flap formed on the sheet and having adhesive means carried thereon for removably adhering the flap to the stem of the handle.

4. The combination of claim 3, wherein each sheet is substantially rectangular in plan outline having top and bottom sides and further having a band of adhesive on one of the sides around the perimeter thereof.

5. The combination of claim 4, wherein each sheet has a forward edge and a rearward edge, and wherein each sheet has a pair of substantially parallel slits formed therein and extending from the forward edge towards the rearward edge, thereby forming the flap on the sheet.

6. In combination with an illumination device intended for medical and/or dental purposes, wherein the illuminated device is provided with a handle, a stack of disposable protective shields removably stacked together, wherein the uppermost shield in the stack may be removed from the stack, each shield being relatively thin and relatively flexible, each shield further being adapted to be manually folded back upon itself and wrapped around the handle, and means carried by each shield for removably securing each shield to the handle, so that the shield will not become separated from the handle of the illumination device during repeated manipulation of the handle during examination and/or treatment of a patient, and wherein the shield may be easily removed from the handle of the illumination device and discarded following examination and/or treatment of a particular patient in the medical or dental office, thereby protecting each patient against exposure to material from a previous patient.

7. In combination with an illumination device intended for medical and/or dental purposes, wherein the illumination device is provided with a handle, a stack of disposable protective shields removably stacked together, wherein a selected shield in the stack may be removed from the stack, each shield being substantially planar and relatively thin and flexible, each shield further being adapted to be manually disposed around the handle, and means carried at least in part by each shield for removably securing each shield to the handle, so that the shield will not become separated from the handle of the illumination device during repeated manipulation of the handle during examination and/or treatment of a patient, and wherein the shield may be removed from the handle of the illumination device and discarded following examination and/or treatment of a particular patient in the medical or dental office, thereby protecting each patient against exposure to material from a previous patient.

* * * * *